(12) United States Patent
Kubo

(10) Patent No.: US 11,523,733 B2
(45) Date of Patent: Dec. 13, 2022

(54) ENDOSCOPE SYSTEM AND METHOD OF OPERATING THE SAME

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 46 days.

(21) Appl. No.: 16/869,895

(22) Filed: May 8, 2020

(65) Prior Publication Data

US 2020/0260942 A1    Aug. 20, 2020

Related U.S. Application Data

(63) Continuation of application No. PCT/JP2018/041288, filed on Nov. 7, 2018.

(30) Foreign Application Priority Data

Nov. 13, 2017   (JP) .............................. JP2017-217889

(51) Int. Cl.
*A61B 1/06*     (2006.01)
*A61B 1/00*     (2006.01)
*A61B 1/313*    (2006.01)

(52) U.S. Cl.
CPC .......... *A61B 1/0653* (2013.01); *A61B 1/0005* (2013.01); *A61B 1/00006* (2013.01); *A61B 1/0676* (2013.01); *A61B 1/3137* (2013.01)

(58) Field of Classification Search
CPC . A61B 1/00045; A61B 1/0005; A61B 1/0017; A61B 1/05; A61B 1/0638; A61B 1/0661; A61B 1/0684; A61B 1/07
See application file for complete search history.

(56) References Cited

U.S. PATENT DOCUMENTS

2006/0209185 A1*   9/2006   Yokoi ................ A61B 1/00016
                                                 348/65
2012/0157775 A1*   6/2012   Yamaguchi ........ A61B 5/14551
                                                 600/180
(Continued)

FOREIGN PATENT DOCUMENTS

CN         1882275 A     12/2006
CN       102613953 A      8/2012
(Continued)

OTHER PUBLICATIONS

An Office Action; "Notice of Reasons for Refusal", mailed by the Japanese Patent Office dated May 11, 2021, which corresponds to Japanese Patent Application No. 2019-552830 and is related to U.S. Appl. No. 16/869,895; with English language translation.

(Continued)

*Primary Examiner* — Michael J Carey
*Assistant Examiner* — Julianna J Nicolaus
(74) *Attorney, Agent, or Firm* — Studebaker & Brackett PC

(57) ABSTRACT

A plurality of kinds of illumination light are emitted while being switched according to a specific light emission pattern. A plurality of observation images, which are obtained from image pickup of an object to be observed illuminated with each illumination light, are acquired. Control to display the plurality of observation images on a display unit while switching the plurality of observation images according to a specific display pattern is performed. The specific light emission pattern is fixed and the specific display pattern is changeable.

12 Claims, 14 Drawing Sheets

(56) References Cited

U.S. PATENT DOCUMENTS

| | | | |
|---|---|---|---|
| 2012/0253158 A1* | 10/2012 | Yamaguchi | A61B 1/0638 600/339 |
| 2013/0245411 A1 | 9/2013 | Saito | |
| 2015/0087903 A1 | 3/2015 | Kuramoto | |
| 2015/0245002 A1* | 8/2015 | Kuramoto | A61B 1/00009 348/70 |
| 2016/0007829 A1 | 1/2016 | Chun | |
| 2016/0296106 A1 | 10/2016 | Shoji | |
| 2017/0112370 A1 | 4/2017 | Daidoji et al. | |
| 2017/0231480 A1* | 8/2017 | Yamazaki | A61B 1/00009 600/476 |
| 2018/0214009 A1 | 8/2018 | Endo | |
| 2019/0117055 A1* | 4/2019 | Ito | A61B 1/05 |
| 2019/0222737 A1 | 7/2019 | Aoyama | |

FOREIGN PATENT DOCUMENTS

| | | | |
|---|---|---|---|
| CN | 102727217 A | | 10/2012 |
| CN | 102860809 A | | 1/2013 |
| CN | 104434000 A | | 3/2015 |
| CN | 105992546 A | | 10/2016 |
| CN | 106535739 A | | 3/2017 |
| CN | 107072508 A | | 8/2017 |
| EP | 2 505 141 A1 | | 10/2012 |
| EP | 3 520 673 A1 | | 8/2019 |
| JP | 2001-149303 A | | 6/2001 |
| JP | 2005-143991 A | | 6/2005 |
| JP | 2012-110485 A | | 6/2012 |
| JP | 2012110485 A | * | 6/2012 |
| JP | 2012-213551 A | | 11/2012 |
| JP | 2013-188364 A | | 9/2013 |
| JP | 2015-159957 A | | 9/2015 |
| JP | 2016-055052 A | | 4/2016 |
| JP | 2016055052 A | * | 4/2016 |
| JP | 2017-185258 A | | 10/2017 |
| WO | 2014/156938 A1 | | 10/2014 |
| WO | 2017/057392 A1 | | 4/2017 |
| WO | 2018/066347 A1 | | 4/2018 |

OTHER PUBLICATIONS

International Search Report issued in PCT/JP2018/041288; dated Jan. 29, 2019.

International Preliminary Report on Patentability issued in PCT/JP2018/041288; completed Dec. 12, 2019.

The extended European search report issued by the European Patent Office dated Dec. 4, 2020, which corresponds to European Patent Application No. 18876807.1-1122 and is related to U.S. Appl. No. 16/869,895.

An Office Action; "Notice of Reasons for Refusal", mailed by the Japanese Patent Office dated Oct. 26, 2021, which corresponds to Japanese Patent Application No. 2019-552830 and is related to U.S. Appl. No. 16/869,895; with English language translation.

An Office Action; "Trial and Appeal Decision", mailed by the Japanese Patent Office dated Jul. 5, 2022, which corresponds to Japanese Patent Application No. 2019-552830 and is related to U.S. Appl. No. 16/869,895; with English language translation.

An Office Action mailed by China National Intellectual Property Administration dated Oct. 9, 2022, which corresponds to Chinese Patent Application No. 201880073237.9 and is related to U.S. Appl. No. 16/869,895; with English language translation.

* cited by examiner

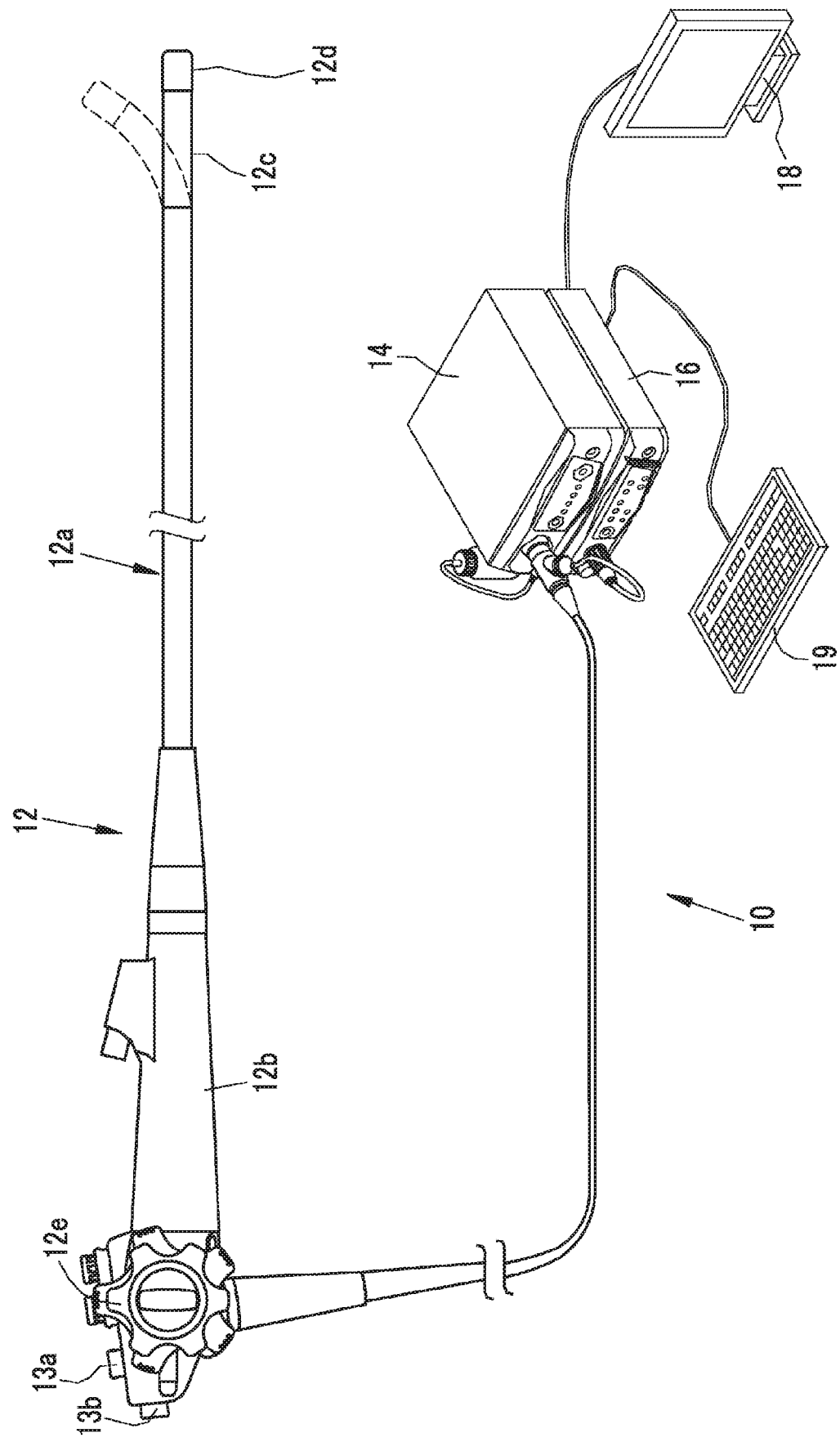

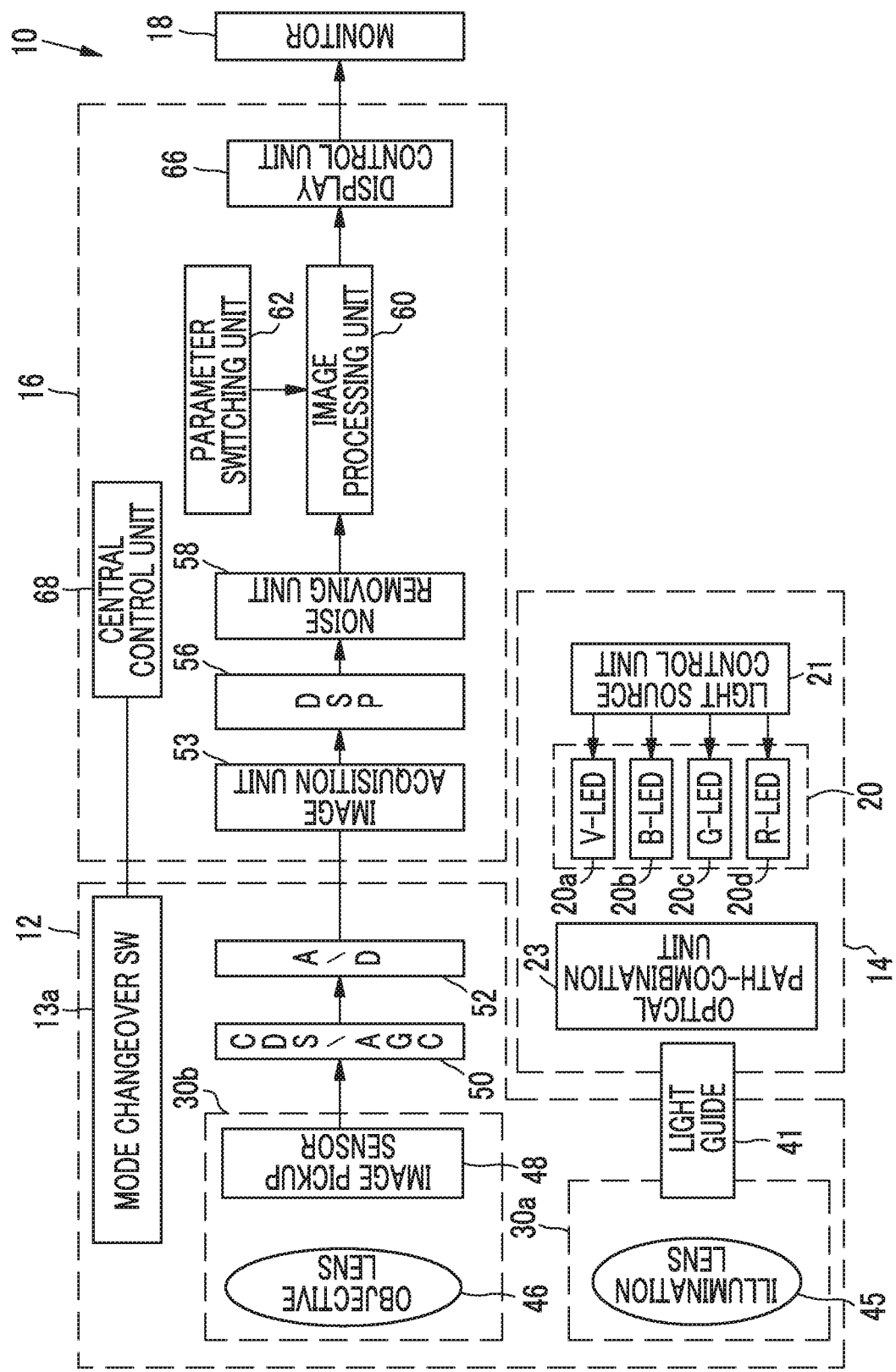

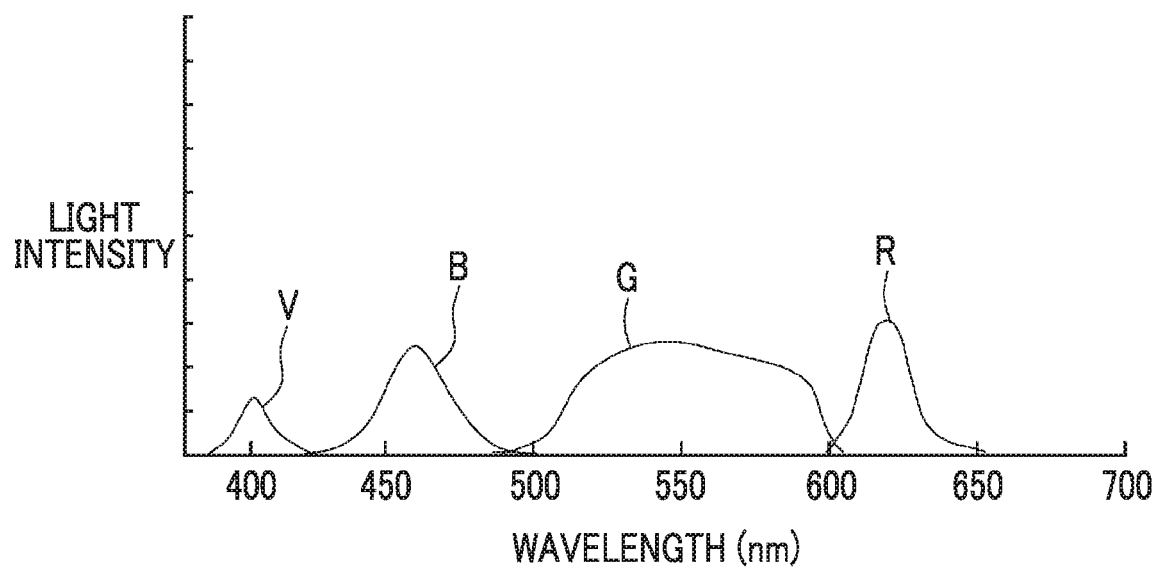
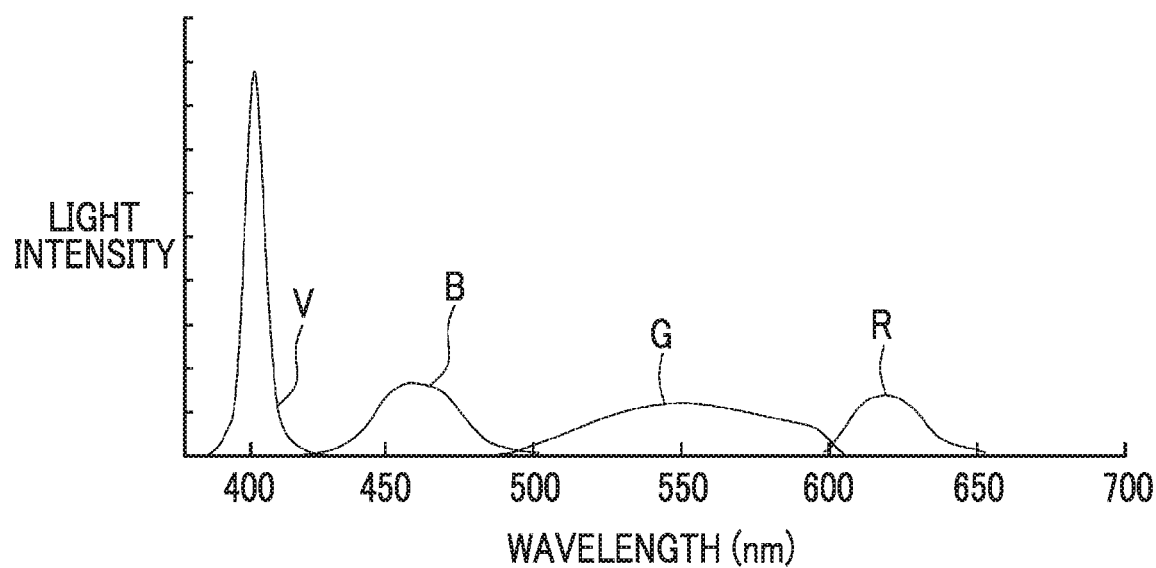

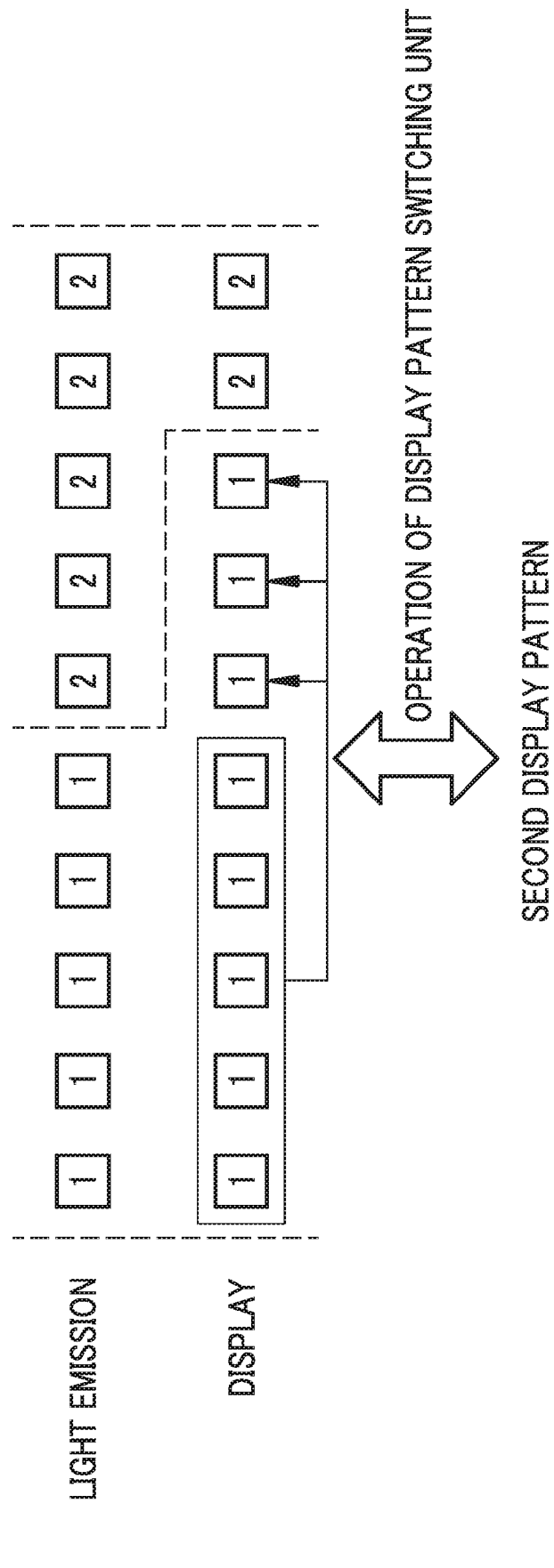
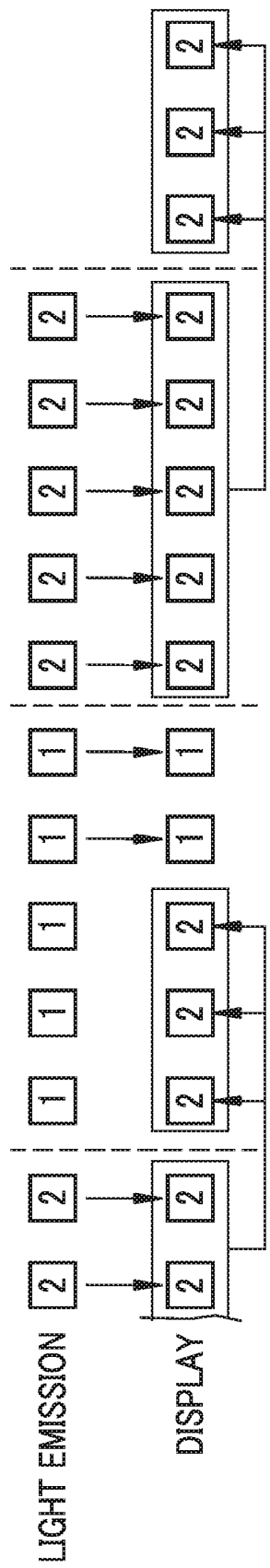
FIG. 12

ENDOSCOPE SYSTEM AND METHOD OF OPERATING THE SAME

CROSS-REFERENCE TO RELATED APPLICATIONS

This application is a Continuation of PCT International Application No. PCT/JP2018/041288 filed on 7 Nov. 2018, which claims priority under 35 U.S.C. § 119(a) to Japanese Patent Application No. 2017-217889 filed on 13 Nov. 2017. The above application is hereby expressly incorporated by reference, in its entirety, into the present application.

BACKGROUND OF THE INVENTION

1. Field of the Invention

The present invention relates to an endoscope system and a method of operating the endoscope system that illuminate an object with a plurality of kinds of illumination light having different wavelength ranges while switching the plurality of kinds of illumination light and display observation images corresponding to the plurality of kinds of illumination light while switching the observation images.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked by an image pickup element of the endoscope.

Further, in recent years, an object to be observed has been illuminated with a plurality of kinds of illumination light having different wavelength ranges to obtain much diagnosis information from the object to be observed. For example, JP2012-213551A (corresponding to US2012/0253158A1) discloses a device that illuminates an object to be observed with wavelength sets formed of narrow-band light having wavelengths of four hundreds nm, five hundreds nm, and six hundreds nm while automatically switching the narrow-band light to allow a user to observe the oxygen saturation of superficial blood vessels, the oxygen saturation of middle-layer blood vessels, and the oxygen saturation of deep blood vessels included in the object to be observed.

SUMMARY OF THE INVENTION

In a case where an object to be observed is illuminated with a plurality of kinds of illumination light having different wavelength ranges as described above, observation images corresponding to the plurality of kinds of illumination light are different from each other in appearance. For example, a blue observation image obtained from illumination using blue light is displayed so that superficial blood vessels are emphasized, but a green observation image obtained from illumination using green light is displayed so that medium-deep blood vessels are emphasized. Since both the superficial blood vessels and the medium-deep blood vessels are important in a diagnosis, a user makes a diagnosis while confirming both the blue observation image and the green observation image.

Here, in a case where a user is to frequently confirm a plurality of observation images, a plurality of kinds of illumination light are automatically switched and observation images corresponding to the plurality of kinds of illumination light are displayed while being automatically switched. Accordingly, a user can confirm the respective observation images without a burden. Further, in a case where a plurality of observation images are to be displayed while being automatically switched as described above, the display contents of each observation image need to be set so that specific subject information (for example, a lesion) included in the object to be observed is emphasized and the other subject information (for example, normal mucous membranes) is not emphasized. Accordingly, the display contents of each observation image need to be capable of being set without applying a load to the entire device to emphasize only specific subject information.

An object of the invention is to provide an endoscope system and a method of operating the endoscope system that can set the display contents of each observation image without applying a load to the entire device to emphasize only specific subject information in a case where a plurality of kinds of illumination light are emitted while being switched and observation images corresponding to the plurality of kinds of illumination light are displayed while being switched.

An endoscope system according to an aspect of the invention comprises a plurality of semiconductor light sources, a light source control unit, an image acquisition unit, and a display control unit. The plurality of semiconductor light sources emit light having wavelength ranges different from each other. The light source control unit controls the plurality of semiconductor light sources. The light source control unit performs control to emit a plurality of kinds of illumination light, which include first illumination light having a first light emission ratio and second illumination light having a second light emission ratio different from the first light emission ratio, while switching the plurality of kinds of illumination light according to a specific light emission pattern. The image acquisition unit acquires a plurality of observation images obtained from image pickup of an object to be observed illuminated with each illumination light. The plurality of observation images include a first observation image corresponding to the first illumination light and a second observation image corresponding to the second illumination light. The display control unit performs control to display the plurality of observation images on a display unit while switching the plurality of observation images according to a specific display pattern. The specific light emission pattern is fixed and the specific display pattern is changeable.

It is preferable that the specific light emission pattern is a pattern where the first illumination light is emitted for a time corresponding to the first number of light emission frames, the first illumination light is then switched to the second illumination light, and the second illumination light is emitted for a time corresponding to the second number of light emission frames in a predetermined specific light emission cycle; the specific display pattern is a pattern where the first observation image is displayed on the display unit for a time corresponding to the first number of display frames, the first observation image is then switched to the second observation image, and the second observation image is displayed on the display unit for a time corresponding to the second number of display frames in the specific light emission cycle; and the first number of light emission frames and the second number of light emission frames are fixed, and the first number of display frames and the second number of display frames are changeable.

It is preferable that, in a case where a first display pattern where the first number of display frames is set to be larger than the second number of display frames is set, a first observation image within a second illumination light-emission period, which is displayed on the display unit in a light emission period of the second illumination light, is displayed on the basis of a first observation image within a first illumination light-emission period that is obtained in a light emission period of the first illumination light prior to the light emission period of the second illumination light.

It is preferable that, in a case where a second display pattern where the first number of display frames is set to be smaller than the second number of display frames is set, a second observation image within a first illumination light-emission period, which is displayed on the display unit in a light emission period of the first illumination light, is displayed on the basis of a second observation image within a second illumination light-emission period that is obtained in a light emission period of the second illumination light prior to the light emission period of the first illumination light. It is preferable that, in a case where a second display pattern where the first number of display frames is set to be smaller than the second number of display frames is set, the first observation image is not displayed on the display unit in a light emission period of the first illumination light.

It is preferable that the endoscope system further comprises a display pattern switching unit that is used to switch a first display pattern where the first number of display frames is set to be larger than the second number of display frames and a second display pattern where the first number of display frames is set to be smaller than the second number of display frames. It is preferable that the display unit displays a switching display screen that displays the plurality of observation images while switching the plurality of observation images and a single-image display screen that displays only any one of the plurality of observation images. It is preferable that, in a case where only any one of the first observation image or the second observation image is displayed in the single-image display screen, the number of display frames of the observation image, which is not displayed in the single-image display screen, of the first and second observation images is set to "0". It is preferable that the display control unit cancels an observation image immediately after switching, which is obtained immediately after switching of each illumination light, not to display the observation image on the display unit.

A method of operating an endoscope system according to another aspect of the invention comprises a light source control step, an image acquisition step, and a display control step. In the light source control step, a light source control unit, which controls a plurality of semiconductor light sources emitting light having wavelength ranges different from each other, performs control to emit a plurality of kinds of illumination light, which include first illumination light having a first light emission ratio and second illumination light having a second light emission ratio different from the first light emission ratio, while switching the plurality of kinds of illumination light according to a specific light emission pattern. In the image acquisition step, an image acquisition unit acquires a plurality of observation images obtained from image pickup of an object to be observed illuminated with each illumination light, and the plurality of observation images include a first observation image corresponding to the first illumination light and a second observation image corresponding to the second illumination light.

In the display control step, a display control unit performs control to display the plurality of observation images on a display unit while switching the plurality of observation images according to a specific display pattern. The specific light emission pattern is fixed and the specific display pattern is changeable.

According to the invention, it is possible to set the display contents of each observation image without applying a load to the entire device to emphasize only specific subject information in a case where a plurality of kinds of illumination light are switched and observation images corresponding to the plurality of kinds of illumination light are displayed while being switched.

BRIEF DESCRIPTION OF THE DRAWINGS

FIG. 1 is a diagram showing the appearance of an endoscope system according to a first embodiment.

FIG. 2 is a block diagram showing the functions of the endoscope system according to the first embodiment.

FIG. 3 is a graph showing the emission spectra of violet light V, blue light B, green light G, and red light R.

FIG. 4 is a graph showing the emission spectrum of first illumination light that includes violet light V, blue light B, green light G, and red light R.

FIG. 12 is a diagram showing that the first display pattern and the second display pattern can be switched to each other.

DESCRIPTION OF THE PREFERRED EMBODIMENTS

Figure 5:
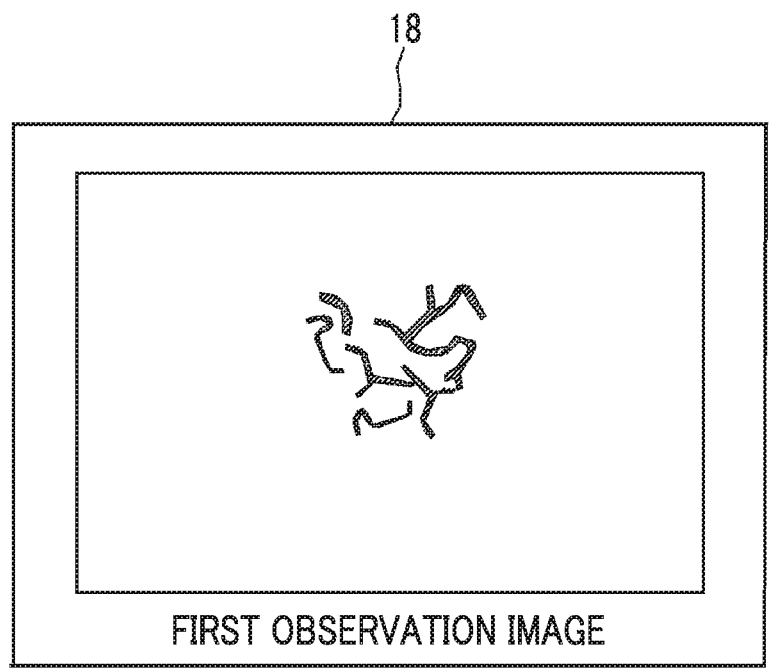
FIG. 5 is an image diagram showing a first observation image.

As shown in FIG. 1, an endoscope system 10 includes an endoscope 12, a light source device 14, a processor device 16, a monitor 18, and a user interface unit 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12*d* faces in a desired direction. A mouse and the like are included in the user interface unit 19 in addition to a keyboard shown in FIG. 1.

Further, the operation part 12*b* is provided with a mode changeover SW 13*a* in addition to the angle knobs 12*e*. The mode changeover SW 13*a* is used for an operating for switching a mode to a normal observation mode, a first special observation mode, a second special observation mode, and a multi-observation mode. The normal observation mode is a mode where a normal image is displayed on the monitor 18. The first special observation mode is a mode where a first observation image where superficial blood vessels are emphasized is displayed on the monitor 18. The second special observation mode is a mode where a second observation image where deep blood vessels are emphasized is displayed on the monitor 18. The first special observation mode and the second special observation mode are automatically switched in the multi-observation mode, so that the first and second observation images are displayed on the monitor 18 while being switched according to a specific display pattern.

A foot switch may be used as a mode switching unit, which is used to switch a mode, other than the mode changeover SW 13*a*. Further, the operation part 12*b* is provided with a freeze button (not shown) that is used to acquire a static image. In a case where a user detects a portion considered to be effective for diagnosis, the mode changeover SW 13*a* and the freeze button are operated alternately.

The processor device 16 is electrically connected to the monitor 18 and the user interface unit 19. The monitor 18 outputs and displays image information and the like. The user interface unit 19 includes a keyboard, a mouse, and the like, and receives an input operation, such as function settings. An external recording unit (not shown), which records image information and the like, may be connected to the processor device 16.

As shown in FIG. 2, the light source device 14 includes a light source unit 20, a light source control unit 21, and an optical path-combination unit 23. The light source unit 20 can emit light having a plurality of wavelength ranges, and can change the light emission ratio of the light having each wavelength range. In this specification, "light having a plurality of wavelength ranges different from each other" means that the plurality of wavelength ranges may partially overlap with each other without meaning that the plurality of wavelength ranges do not overlap with each other at all. The light source unit 20 includes a violet light emitting diode (V-LED) 20*a*, a blue light emitting diode (B-LED) 20*b*, a green light emitting diode (G-LED) 20*c*, and a red light emitting diode (R-LED) 20*d* to emit light having a plurality of wavelength ranges. Since it is preferable that the light source unit 20 is provided with a plurality of semiconductor light sources, a laser diode (LD) may be used instead of the LED.

The light source control unit 21 controls the drive of the LEDs 20*a* to 20*d*. The optical path-combination unit 23 combines the optical paths of pieces of light that are emitted from the four color LEDs 20*a* to 20*d* and have four colors. The inside of an object to be examined is irradiated with the pieces of light, which are combined by the optical path-combination unit 23, through a light guide 41 inserted into the insertion part 12*a* and an illumination lens 45.

As shown in FIG. 3, the V-LED 20*a* generates violet light V of which the central wavelength is in the range of 405±10 nm and the wavelength range is in the range of 380 to 420 nm. The B-LED 20*b* generates blue light B of which the central wavelength is in the range of 460±10 nm and the wavelength range is in the range of 420 to 500 nm. The G-LED 20*c* generates green light G of which the wavelength range is in the range of 480 to 600 nm. The R-LED 20*d* generates red light R of which the central wavelength is in the range of 620 to 630 nm and the wavelength range is in the range of 600 to 650 nm.

The light source control unit 21 performs control to turn on the V-LED 20*a*, the B-LED 20*b*, the G-LED 20*c*, and the R-LED 20*d* in all observation modes. Further, the light source control unit 21 controls the respective LEDs 20*a* to 20*d* so that normal light of which the light intensity ratios of violet light V, blue light B, green light G, and red light R are Vc:Bc:Gc:Rc is emitted in the normal observation mode. In this specification, a light emission ratio means the light intensity ratio of each semiconductor light source and includes a case where the light intensity ratio is 0 (zero). Accordingly, the light emission ratio includes a case where any one or two of the respective semiconductor light sources are not turned on. For example, even in a case where only one semiconductor light source is turned on and the other three semiconductor light sources are not turned on as in a case where the light intensity ratios of violet light V, blue light B, green light G, and red light R are 1:0:0:0, it is considered that the light source unit has a light emission ratio.

Furthermore, in the first special observation mode, the light source control unit 21 controls the respective LEDs 20*a* to 20*d* to emit first illumination light of which the light emission ratios of violet light V, blue light B, green light G, and red light R are Vs1:Bs1:Gs1:Rs1. It is preferable that the first illumination light has a peak in the range of 400 nm to 440 nm. For this purpose, Vs1:Bs1:Gs1:Rs1 of the first illumination light are set so that the light intensity of violet light V is higher than the light intensity of each of blue light B, green light G, and red light R as shown in FIG. 4 (Vs1>Bs1, Gs1, and Rs1). In a case where the image of an object to be observed illuminated with the first illumination light is picked up, a first observation image where superficial blood vessels are emphasized as shown in FIG. 5 is obtained.

Further, since the first illumination light includes a first red-light wavelength range like red light R, the first illumination light can accurately reproduce the color of a mucous membrane. Furthermore, since the first illumination light includes a first blue-light wavelength range and a first green-light wavelength range like violet light V, blue light B, and green light G, the first illumination light can also emphasize various structures, such as glandular structures and unevenness, in addition to the above-mentioned superficial blood vessels.

Moreover, in the second special observation mode, the light source control unit 21 controls the respective LEDs 20*a* to 20*d* to emit second illumination light of which the light emission ratios of violet light V, blue light B, green light G, and red light R are Vs2:Bs2:Gs2:Rs2. It is preferable that the intensity ratio of the second illumination light is higher than that of the first illumination light at wavelengths of 460 nm, 540 nm, and 630 nm.

Figure 6:
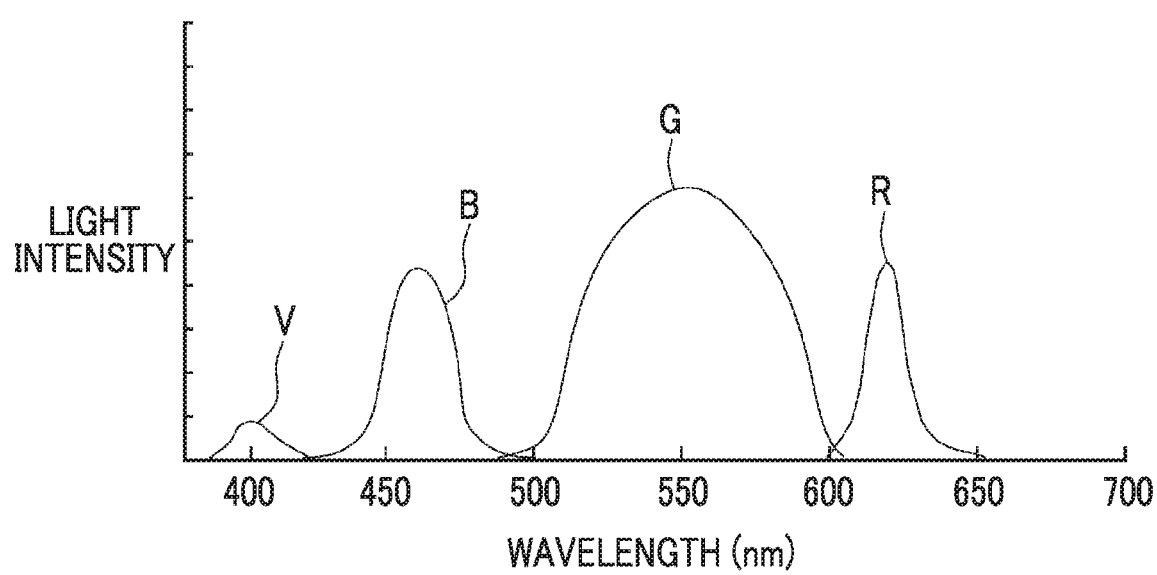
FIG. 6 is a graph showing the emission spectrum of second illumination light that includes violet light V, blue light B, green light G, and red light R.
Figure 7:
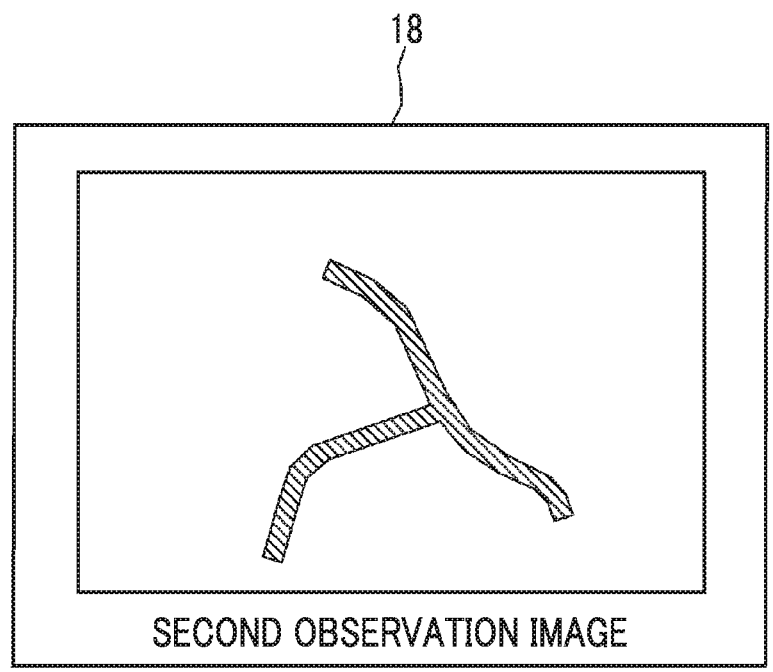
FIG. 7 is an image diagram showing a second observation image.

For this purpose, Vs2:Bs2:Gs2:Rs2 of the second illumination light are set so that the amounts of blue light B, green light G, and red light R of the second illumination light are larger than the amounts of blue light B, green light G, and red light R of the first illumination light as shown in FIG. 6. In a case where the image of an object to be observed illuminated with the second illumination light is picked up, a second observation image where medium-deep blood vessels are emphasized as shown in FIG. 7 is obtained.

Vs2:Bs2:Gs2:Rs2 are set so that the light intensity of violet light V is lower than the light intensity of each of blue light B, green light G, and red light R (Vs2<Bs2, Gs2, and Rs2). Further, since the second illumination light includes a second red-light wavelength range like red light R, the second illumination light can accurately reproduce the color of a mucous membrane. Furthermore, since the second illumination light includes a second blue-light wavelength range and a second green-light wavelength range like violet light V, blue light B, and green light G, the second illumination light can also emphasize various structures, such as glandular structures and unevenness, in addition to the above-mentioned medium-deep blood vessels.

Further, in a case where a mode is set to the multi-observation mode, the light source control unit 21 performs control to emit the first illumination light and the second illumination light while automatically switching the first illumination light and the second illumination light according to a specific light emission pattern. The specific light emission pattern is a pattern where the first illumination light is emitted for a time corresponding to the first number of light emission frames, the first illumination light is then switched to the second illumination light, and the second illumination light is emitted for a time corresponding to the second number of light emission frames in a predetermined specific light emission cycle. Here, in this embodiment, a light emission time where illumination light is emitted is represented by a value converted into the number of frames that is a unit used for the control of an image pickup sensor 48 (see FIG. 2) picking up the image of an object to be observed. Accordingly, the light emission time of the first illumination light in the specific light emission cycle is represented as a time of "the first number of light emission frames" minutes, and the light emission time of the second illumination light is represented as a time of "the second number of light emission frames" minutes. In a case where a plurality of kinds of illumination light are emitted while being switched, the light emission order of the plurality of kinds of illumination light is included in the specific light emission pattern in addition to the light emission times of the plurality of kinds of illumination light.

The first number of light emission frames and the second number of light emission frames in the above-mentioned specific light emission cycle are fixed. Here, "fixed" means that a specific light emission pattern cannot be changed by a user after the specific light emission pattern, such as the light emission order of the first illumination light and the second illumination light in addition to the first number of light emission frames and the second number of light emission frames, is set at the time of the shipment of the light source device 14 from the factory. For example, a user cannot change the specific light emission pattern in a case where the endoscope 12 is used, that is, in a case where the light source device 14 to which the endoscope 12 is to be connected is used. However, the change of the specific light emission pattern, which is performed by a person authorized to change the specific light emission pattern, such as the administrator of the light source device 14, is not hindered. Further, each of the numbers of light emission frames is set to a period of two or more frames. The reason why each of the numbers of light emission frames is set to a period of two or more frames as described above is that the illumination light of the light source device 14 is immediately switched but the image processing of the processor device 16 has at least two or more frames without being immediately switched.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of φ 0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 corresponds to a medical image processing device that processes medical images, such as images obtained by the endoscope 12. The processor device 16 comprises an image acquisition unit 53, a digital signal processor (DSP) 56, a noise removing unit 58, an image processing unit 60, a parameter switching unit 62, a display control unit 66, and a central control unit 68. Digital color image signals output from the endoscope 12 are input to the image acquisition unit 53. The color image signals are RGB image signals formed of R-image signals that are output from the R-pixels of the image pickup sensor 48, G-image signals that are output from the G-pixels of the image pickup sensor 48, and B-image signals that are output from the B-pixels of the image pickup sensor 48.

The DSP 56 performs various kinds of signal processing, such as defect correction processing, offset processing, gain processing, color adjustment processing, gamma conversion processing, and demosaicing processing, on the received image signals. Signals of defective pixels of the image pickup sensor 48 are corrected in the defect correction processing. Dark current components are removed from the RGB image signals having been subjected to the defect correction processing in the offset processing, so that an accurate zero level is set.

The RGB image signals having been subjected to the offset processing are multiplied by a specific gain parameter in the gain processing, so that signal levels are adjusted. The specific gain parameter varies for each observation mode. For example, gain processing for normal light for multiplying image signals, which are obtained from the illumination of the normal light and image pickup, by a gain parameter for normal light as the specific gain parameter is performed in the normal observation mode. Further, gain processing for first illumination light for multiplying RGB image signals (first observation image), which are obtained from the illumination of the first illumination light and image pickup, by a gain parameter for first illumination light as the specific gain parameter is performed in the first special observation mode. Furthermore, gain processing for second illumination light for multiplying RGB image signals (second observation image), which are obtained from the illumination of the second illumination light and image pickup, by a gain parameter for second illumination light as the specific gain parameter is performed in the second special observation mode.

Further, in the multi-observation mode, the gain processing for first illumination light is performed on RGB image signals, which are obtained from the illumination of the first illumination light and image pickup, at the time of the illumination of the first illumination light, and the gain processing for second illumination light is performed on RGB image signals, which are obtained from the illumination of the second illumination light and image pickup, at the time of the illumination of the second illumination light.

After that, brightness or a saturation is adjusted by the gamma conversion processing. The demosaicing processing (also referred to as equalization processing or demosaicing) is performed on the RGB image signals having been subjected to the color adjustment processing, so that signals of colors deficient in each pixel are generated by interpolation. All the pixels are made to have the signals of the respective colors of R, G, and B by this demosaicing processing.

The noise removing unit 58 performs noise removal processing (for example, a moving-average method, a median filtering method, or the like) on the RGB image signals, which have been subjected to gamma correction and the like by the DSP 56, to remove noise from the RGB image signals. The RGB image signals from which noise has been removed are transmitted to the image processing unit 60.

The image processing unit 60 performs various kinds of image processing on the RGB image signals. The various kinds of image processing include image processing that is performed under a condition varying for each observation mode in addition to image processing that is performed under the same condition regardless of an observation mode. The image processing that is performed under a condition varying for each observation mode includes color adjustment processing for improving color reproducibility and structure emphasis processing for emphasizing various structures, such as blood vessels and unevenness. Each of the color adjustment processing and the structure emphasis processing is processing that uses a two-dimensional look up table (LUT), a three-dimensional look up table (LUT), a matrix, or the like. In a case where the color emphasis processing and the structure emphasis processing are to be performed, a color emphasis processing parameter and a structure emphasis processing parameter set for each observation mode are used in the image processing unit 60. The switching of the color emphasis processing parameter or the structure emphasis processing parameter is performed by the parameter switching unit 62.

In a case where a mode is set to the normal observation mode, a parameter to be used in the image processing unit 60 is switched to a color emphasis processing parameter for normal light and a structure emphasis processing parameter for normal light by the parameter switching unit 62. Then, the image processing unit 60 performs color emphasis processing for normal light on the RGB image signals using the color emphasis processing parameter for normal light, and performs structure emphasis processing for normal light on the RGB image signals using the structure emphasis processing parameter for normal light. After that, the RGB image signals having been subjected to the above-mentioned processing are input to the display control unit 66 as the normal image.

In a case where a mode is set to the first special observation mode, a parameter to be used in the image processing unit 60 is switched to a color emphasis processing parameter for first illumination light and a structure emphasis processing parameter for first illumination light by the parameter switching unit 62. Then, the image processing unit 60 performs color emphasis processing for first illumination light on the RGB image signals using the color emphasis processing parameter for first illumination light, and performs structure emphasis processing for first illumination light on the RGB image signals using the structure emphasis processing parameter for first illumination light. After that, the RGB image signals having been subjected to the above-mentioned processing are input to the display control unit 66 as the first observation image.

In a case where a mode is set to the second special observation mode, a parameter to be used in the image processing unit 60 is switched to a color emphasis processing parameter for second illumination light and a structure emphasis processing parameter for second illumination light by the parameter switching unit 62. Then, the image processing unit 60 performs color emphasis processing for second illumination light on the RGB image signals using the color emphasis processing parameter for second illumination light, and performs structure emphasis processing for second illumination light on the RGB image signals using the structure emphasis processing parameter for second illumination light. After that, the RGB image signals having been subjected to the above-mentioned processing are input to the display control unit 66 as the second observation image.

In a case where a mode is set to the multi-observation mode, the image processing unit 60 performs the color emphasis processing for first illumination light and the structure emphasis processing for first illumination light on the RGB image signals at the time of the illumination of the first illumination light. After that, the RGB image signals having been subjected to the above-mentioned processing are input to the display control unit 66 as the first observation image. Further, the image processing unit 60 performs the color emphasis processing for second illumination light and the structure emphasis processing for second illumination light on the RGB image signals at the time of the illumination of the second illumination light. Furthermore, in a case where a mode is set to the multi-observation mode, the image processing unit 60 performs mucous membrane-color-balance processing for setting the colors of normal mucous membranes, which are included in the object to be observed, to the same color between the first observation image and the second observation image. First mucous membrane-color-balance processing is performed on the first observation image, and second mucous membrane-color-balance processing based on the result of the first mucous membrane-color-balance processing is performed on the second observation image. After that, the RGB image signals having been subjected to the above-mentioned processing are input to the display control unit 66 as the second observation image.

B1-image signals, G1-image signals, and R1-image signals included in the first observation image are automatically adjusted in the first mucous membrane-color-balance processing as described in, for example, D1) to D3) to be described below so that the average color of the entire screen has a specific color balance. The first mucous membrane-color-balance processing is performed on the assumption that the color of a mucous membrane is dominant over the object to be observed. Then, the first mucous membrane-color-balance processing is performed, so that B1*-image signals, G1*-image signals, and R1*-image signals having been subjected to the first mucous membrane-color-balance processing are obtained.

$$B1^*\text{-image signal} = B1/B1\text{ave} \tag{D1}$$

$$G1^*\text{-image signal} = G1/G1\text{ave} \tag{D2}$$

$$R1^*\text{-image signal} = R1/R1\text{ave} \tag{D3}$$

Here, B1ave denotes the average pixel value of the B1-image signals (the sum of pixel values of the entire screen (effective pixels)/the number of effective pixels). G1ave denotes the average pixel value of the G1-image signals (the sum of pixel values of the entire screen (effective pixels)/the number of effective pixels). R1ave denotes the average pixel value of the R1-image signals (the sum of pixel values of the entire screen (effective pixels)/the number of effective pixels).

Further, B2-image signals, G2-image signals, and R2-image signals included in the second observation image are automatically adjusted in the second mucous membrane-color-balance processing as described in, for example, E1) to E3) to be described below so that the average color of the entire screen has a specific color balance. B1ave, G1ave, and R1ave calculated in the first mucous membrane-color-balance processing are used in the second mucous membrane-color-balance processing. Then, the second mucous membrane-color-balance processing is performed, so that B2*-image signals, G2*-image signals, and R2*-image signals having been subjected to the second mucous membrane-color-balance processing are obtained.

$$B2^*\text{image signal} = B2/B1\text{ave} \tag{E1}$$

$$G2^*\text{image signal} = G2/G1\text{ave} \tag{E2}$$

$$R2^*\text{image signal} = R2/R1\text{ave} \tag{E3}$$

The display control unit 66 performs control to display the normal image, the first observation image, or the second observation image, which is input from the image processing unit 60, as an image that can be displayed on the monitor 18. In the normal observation mode, the display control unit 66 displays the normal image on the monitor 18. In the first special observation mode, the display control unit 66 displays the first observation image on the monitor 18. In the second special observation mode, the display control unit 66 displays the second observation image on the monitor 18. In the multi-observation mode, the display control unit 66 displays the first observation image or the second observation image on the monitor 18 while switching the first and second observation images according to a specific display pattern. The details of display control in the multi-observation mode will be described later.

The central control unit 68 controls the respective parts of the processor device 16. Further, the central control unit 68 receives information from the endoscope 12 or the light source device 14, and performs the control of the respective parts of the processor device 16 and the control of the endoscope 12 or the light source device 14 on the basis of the received information.

Figure 8:
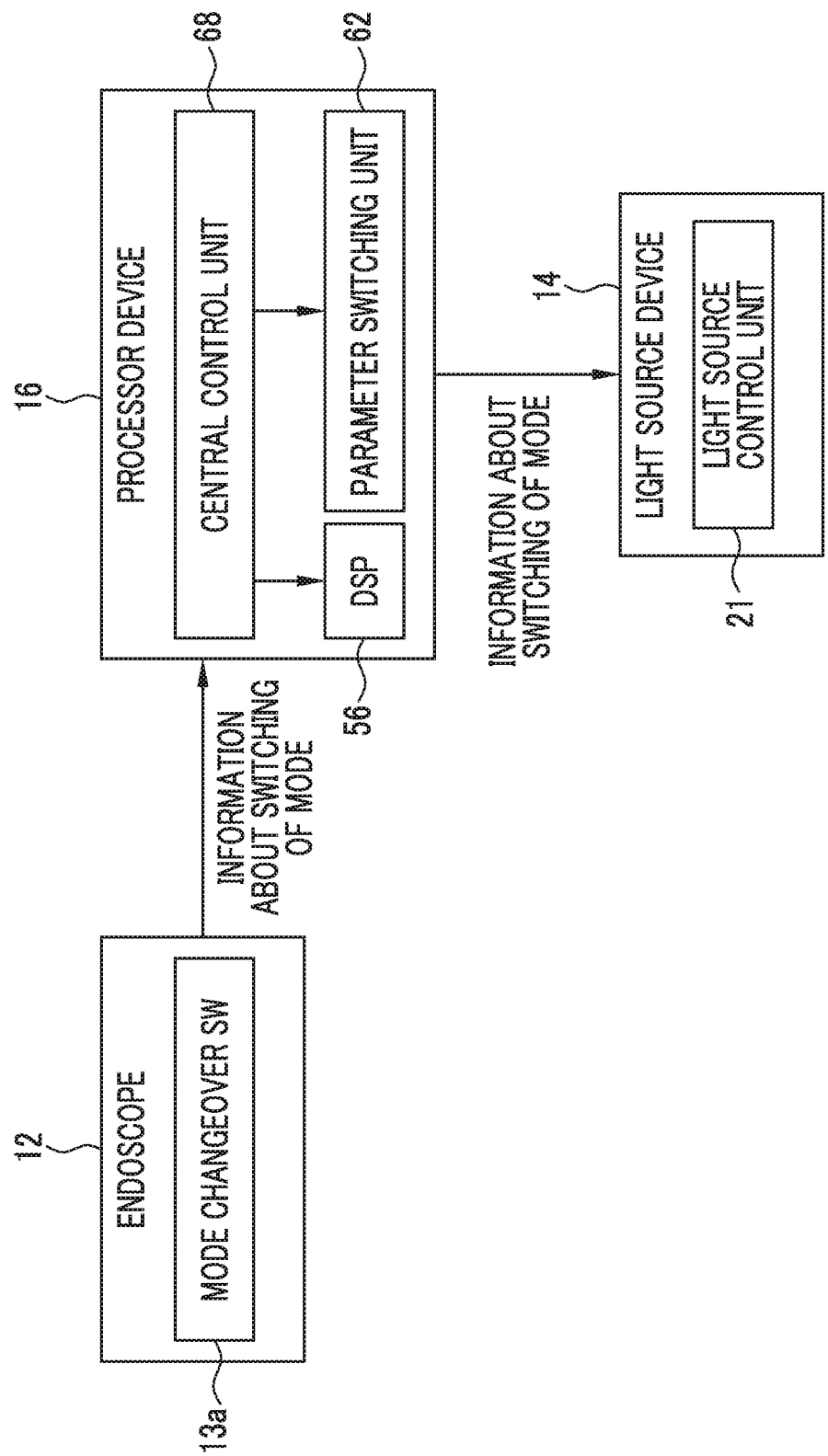
FIG. 8 is a block diagram showing the flow of information in a case where a mode is switched.

For example, in a case where an observation mode is switched in the endoscope 12, information about the switching of a mode is transmitted to the central control unit 68 as shown in FIG. 8. In a case where the central control unit 68 receives the information about the switching of a mode, the central control unit 68 instructs the light source device 14 to emit light corresponding to a switched mode. In the light source device 14, the light source control unit 21 changes the light emission ratio of light to be emitted from the light source unit 20 to emit light corresponding to the switched mode in a case where the light source control unit 21 receives an instruction to emit light corresponding to the switched mode. The light source control unit 21 can control the light sources in response to an instruction from the central control unit 68 while hardly requiring time. For example, the light source control unit 21 changes the light emission ratio in less than one frame after a mode is switched.

Further, in a case where the central control unit 68 receives information about the switching of a mode, the central control unit 68 instructs the DSP 56 or the parameter switching unit 62 provided in the processor device 16 to change processing according to the switching of a mode. For example, in a case where a mode is switched to the second special observation mode from the first special observation mode, the DSP 56 switches gain processing to the gain processing for second illumination light from the gain processing for first illumination light by switching a gain parameter to the gain parameter for second illumination light from the gain parameter for first illumination light. Further, the parameter switching unit 62 switches color adjustment processing to color adjustment processing for second illumination light from color adjustment processing for first illumination light by switching a color adjustment processing parameter to a color adjustment processing parameter for second illumination light from a color adjustment processing parameter for first illumination light. Furthermore, the parameter switching unit 62 switches structure emphasis processing to the structure emphasis processing for second illumination light from the structure emphasis processing for first illumination light by switching a structure emphasis processing parameter to the structure emphasis processing parameter for second illumination light from the structure emphasis processing parameter for first illumination light.

The switching of the gain processing, the color adjustment processing, and the like having been described above is often not performed immediately due to a processing situation or the like in the processor device 16. For example, there is a case where two or more frames are required after a mode is switched until gain processing, color adjustment processing, and the like are completely switched to the gain processing, the color adjustment processing, and the like corresponding to the switched mode. Accordingly, it is preferable that the number of frames is set to two or more.

In the multi-observation mode, the display control of a plurality of observation images is performed according to a specific display pattern. The specific display pattern is a pattern where the first observation image is displayed on the monitor 18 for a time corresponding to the first number of display frames, the first observation image is then switched to the second observation image, and the second observation image is displayed on the monitor 18 for a time corresponding to the second number of display frames in the specific light emission cycle. Here, in this embodiment, a time where the observation image is displayed on the monitor 18 is represented by a value converted into the number of frames that is a unit used for the control of the image pickup sensor 48 (see FIG. 2) picking up the image of an object to be observed. Accordingly, the display time of the first observation image in the specific light emission cycle is represented as a time of "the first number of light emission frames" minutes, and the display time of the second observation image is represented as a time of "the second number of display frames" minutes. In a case where a plurality of observation images are displayed while being switched, the display order of the respective observation images is included in the specific display pattern in addition to the display times of the respective observation images.

Figure 9:
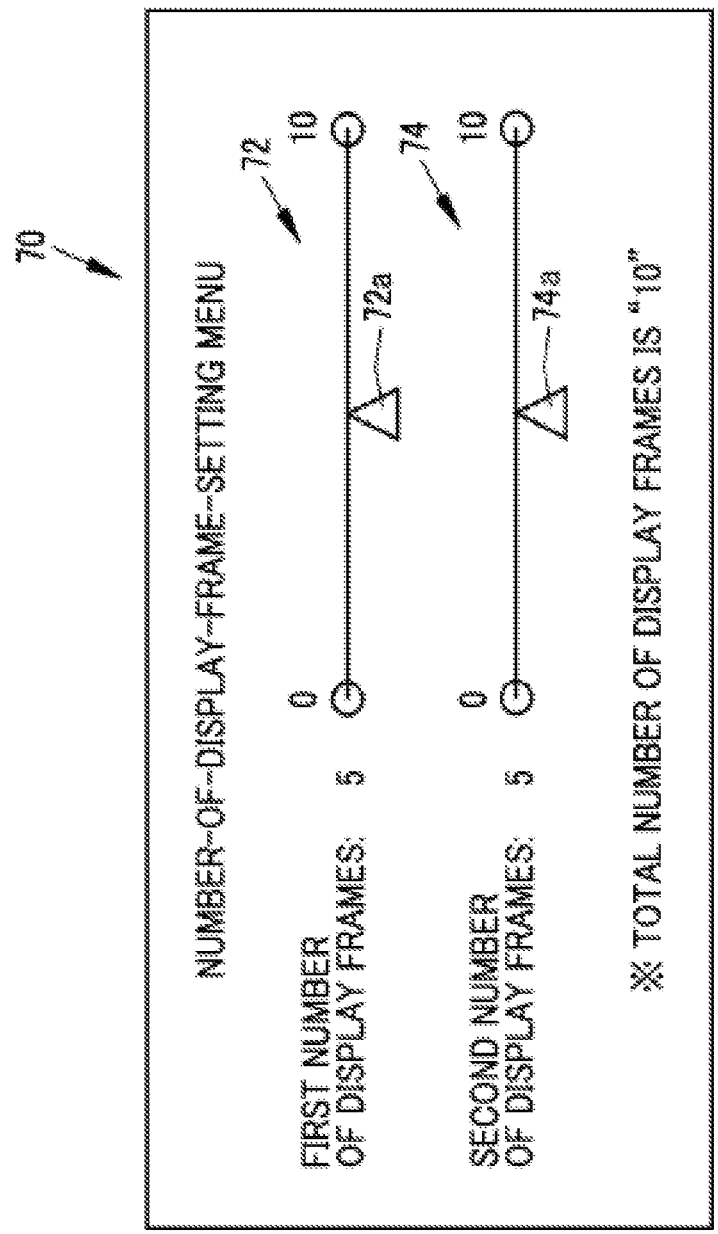
FIG. 9 is a diagram showing a number-of-display-frame-setting menu.

The first number of display frames or the second number of display frames can be changed by a user, and the change of each of the numbers of display frames is performed in a number-of-display-frame-setting menu 70 shown in FIG. 9. Information about the change of each of the numbers of display frames performed in the number-of-display-frame-setting menu 70 is sent to the display control unit 66.

Here, the first number of display frames and the second number of display frames are determined so that a difference in specific subject information (for example, blood vessel portions) included in the first and second observation images can be emphasized. Here, in a case where each of the first and second observation images is displayed for a relatively long time and are switched, there is a case where it is difficult to notice a difference between these images, particularly, a difference between blood vessels. Further, in a case where the first number of display frames or the second number of display frames is reduced so that the first and second observation images are displayed while being switched at a high speed in a short time, the first and second observation images are recognized as not two kinds of observation images but one kind of observation image. Accordingly, it is preferable that each of the first number of display frames and the second number of display frames is set to a predetermined number of frames or more (for example, three or more frames) so that a difference in specific subject information of two kinds of images can be emphasized and the first and second observation images are not recognized as one kind of image.

Furthermore, in a case where the first number of display frames and the second number of display frames are set to be equal to each other so that the first and second observation images are displayed for the same display time while being switched, the first and second observation images may flicker. For this reason, one of the first number of display frames and the second number of display frames is set to be long and the other thereof is set to be short, so that the first and second observation images can be displayed while a difference between the first and second observation images is emphasized. In a case where a third observation image obtained on the basis of third illumination light having a wavelength range between the wavelength of the first illumination light and the wavelength of the second illumination light is displayed while being switched in addition to the first observation image or the second observation image, blood vessels extending to a superficial layer from a medium-deep layer can be made to be three-dimensionally displayed. In this case, for example, it is preferable that the number of display frames of an observation image (for example, the first observation image) serving as a base is set to be large and the third observation image where blood vessels extending to a superficial layer from a medium-deep layer are emphasized and the second observation image where medium-deep blood vessels are emphasized are sequentially displayed by a small number of frames.

The first number of display frames can be changed between, for example, "0" and "10". In a case where the first number of display frames is to be changed, a user operates the user interface unit 19 to move a slider 72a to the left side or the right side on a slide bar 72 representing the first number of display frames. As a result, the first number of display frames is changed. Further, the second number of display frames can also be changed between "0" and "10" as with the first number of display frames. Even in a case where the second number of display frames is to be changed, a user operates the user interface unit 19 to move a slider 74a to the left side or the right side on a slide bar 74 representing the second number of display frames. As a result, the second number of display frames is changed. In the case of the slide bar 72, the first number of display frames is larger as the slider is closer to the right side. The same applies to the slide bar 74.

However, the total number of display frames, which is the sum of the first number of display frames and the second number of display frames in the specific light emission cycle, is fixed. For example, the total number of display frames is fixed to "10". Accordingly, in a case where one of the first number of display frames and the second number of display frames is increased, the other thereof is reduced by an increase in one of the first number of display frames and the second number of display frames. For example, in a case where the total number of display frames is set to "10" and the first number of display frames is changed to "8", the second number of display frames is changed to "2" with a change in the first number of display frames.

Further, in this embodiment, the first number of light emission frames or the second number of light emission frames is not changed to be fixed and only the first number of display frames or the second number of display frames is changed. Here, in a case where not only the first number of display frames or the second number of display frames but also the first number of light emission frames or the second number of light emission frames is to be changed, the light emission timing of the illumination light of the light source device 14 and the processing timing of the image processing of the processor device 16 need to be synchronized with each other. However, since the time required to change the light emission timing of the illumination light and the time required to change the processing timing of the image processing are different from each other, a certain time or more is required to synchronize these times. For this reason, a load is applied to the processor device 16 and the like. Further, in a case where the light emission timing of the illumination light is changed on a frame basis, there is a possibility that image processing may become complicated. Accordingly, since the first number of light emission frames or the second number of light emission frames is not changed to be fixed and only the first number of display frames or the second number of display frames is changed in this embodiment, a load is not applied to the processor device 16 and the like.

Figure 10:
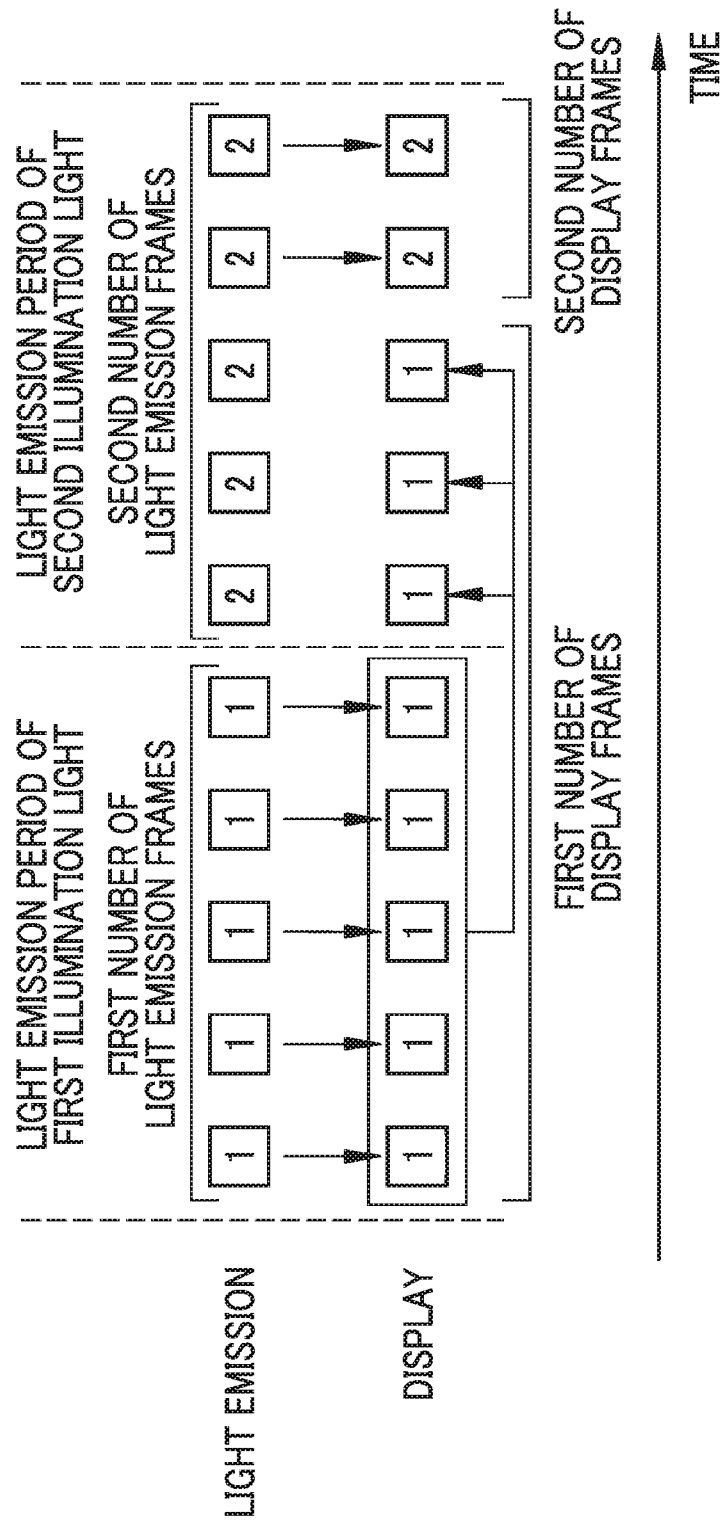
FIG. 10 is a diagram showing a first display pattern.

In a case where the first number of display frames or the second number of display frames is changed, the display control unit 66 performs control to display each observation image by each of the changed numbers of display frames. Here, in a case where the first number of display frames is set to "8" and the second number of display frames is set to "2" as a first display pattern where the first number of display frames is set to be larger than the second number of display frames as shown in FIG. 10, the first observation images are displayed for the time of all the five frames in the light emission period of the first illumination light. Then, the first observation images are displayed and the second observation images are not displayed for the time of the first three frames in the light emission period of the second illumination light next to the light emission period of the first illumination light. After that, the second observation images are displayed for the time of the last two frames in the light emission period of the second illumination light.

In FIG. 10, rectangular boxes arranged next to "light emission" represent light emission frames at certain times, "1" in the box represents the light emission of the first illumination light, and "2" in the box represents the light emission of the second illumination light. Further, rectangular boxes arranged next to "display" represent display frames at certain times, "1" in the box represents the display of the first observation image, and "2" in the box represents the display of the second observation image.

Here, the first observation images displayed in the light emission period of the second illumination light (the first observation images within a second illumination light-emission period) are displayed on the basis of the first observation images within a first illumination light-emission period that are obtained in the light emission period of the first illumination light prior to the light emission period of the second illumination light. For example, the first observation image within the second illumination light-emission period may be the first observation image obtained at the last fifth frame among the first observation images within the first illumination light-emission period of five frames. Further, the first observation image within the second illumination light-emission period may be an image that is obtained from the combination of the first observation images within the first illumination light-emission period of five frames. Furthermore, the first observation images within the second illumination light-emission period may be the same image or may be different images for all the three frames.

Figure 11:
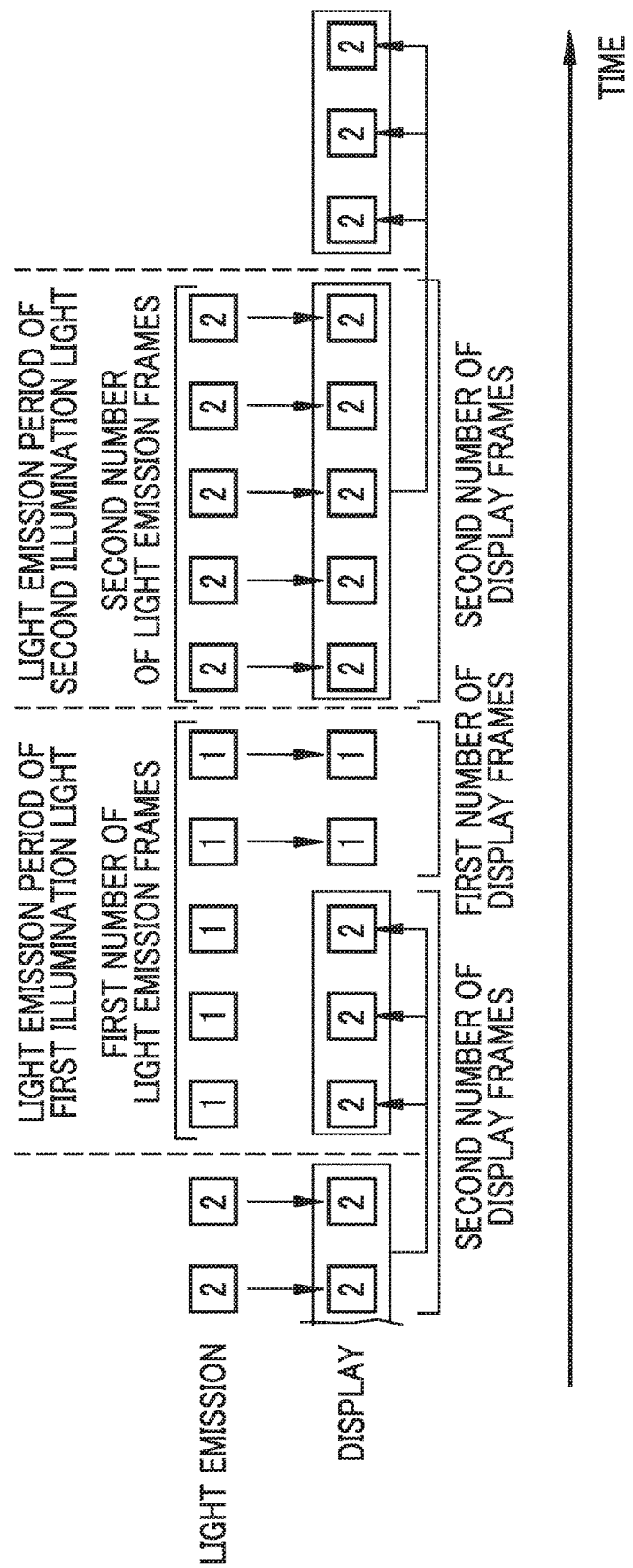
FIG. 11 is a diagram showing a second display pattern.

On the other hand, in a case where the first number of display frames is set to "2" and the second number of display frames is set to "8" as a second display pattern where the first number of display frames is set to be smaller than the second number of display frames as shown in FIG. 11, the second observation images are displayed and the first observation images are not displayed for the time of the first three frames in the light emission period of the first illumination light. Then, the first observation images are displayed for the time of the last two frames in the light emission period of the first illumination light. After that, the second observation images are displayed for the time of all the five frames in the light emission period of the second illumination light.

Here, it is preferable that the second observation images displayed in the light emission period of the first illumination light (the second observation images within the first illumination light-emission period) are generated on the basis of the second observation images within the second illumination light-emission period obtained in the light emission period of the second illumination light prior to the light emission period of the first illumination light and are displayed prior to the first observation images in the first illumination light-emission period. For example, it is preferable that the second observation image within the first illumination light-emission period may be generated on the basis of the second observation image obtained at the last fifth frame among the second observation images within the second illumination light-emission period. Further, the second observation image within the first illumination light-emission period may be an image that is obtained from the combination of all or some of images obtained in the second observation images within the second illumination light-emission period. Furthermore, the second observation images within the first illumination light-emission period may be the same image or may be different images for all the three frames.

The above-mentioned first and second display patterns (see FIGS. 10 and 11) may be adapted to be capable of being switched as shown in FIG. 12 by a user. For this purpose, the operation part 12b of the endoscope is provided with a display pattern switching unit 13b (see FIG. 1) that is used to switch a display pattern to any one of the first display pattern or the second display pattern. In a case where a user operates the display pattern switching unit 13b, the user can switch a display pattern to a display pattern desired by the user.

Figure 13:
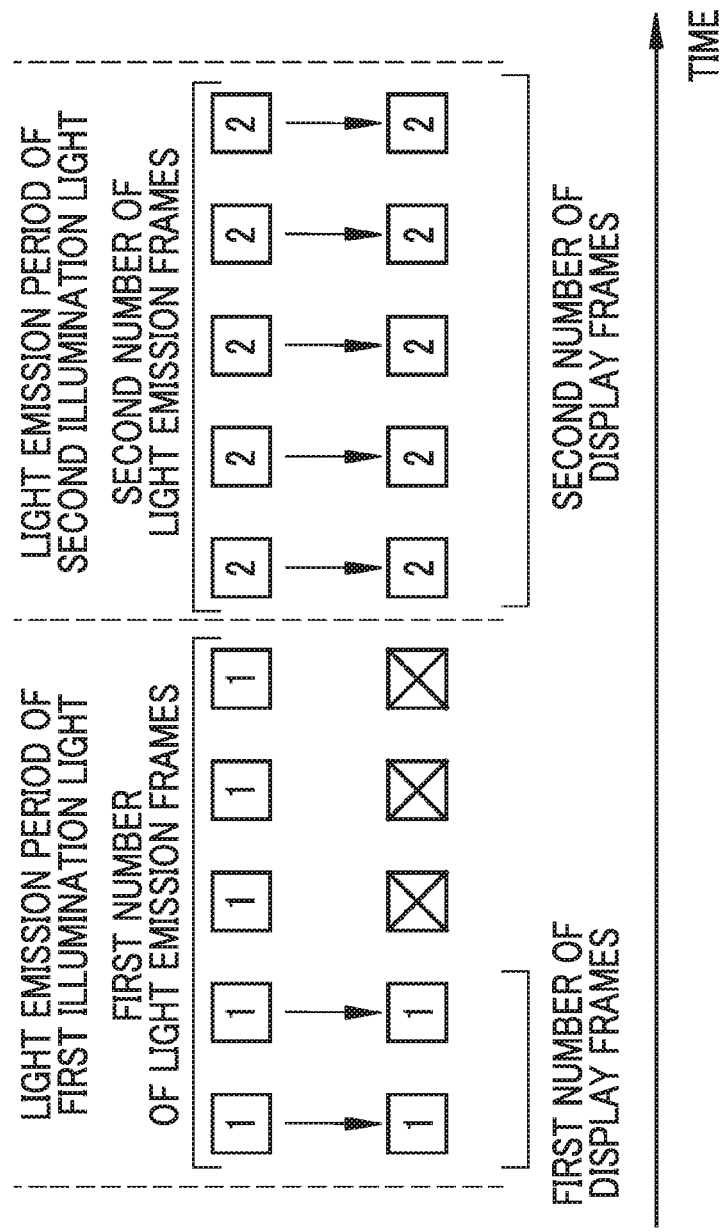
FIG. 13 is a diagram showing an aspect where a first observation image and a second observation image are displayed in a case where the first number of display frames is reduced.

Further, in the above description, in a case where one of the first number of display frames and the second number of display frames is reduced, the other thereof has been increased by a reduction in one of the first number of display frames and the second number of display frames. However, the invention is not limited thereto. For example, in a case where the first number of display frames is reduced to "2" from "5" as shown in FIG. 13, the second number of display frames is maintained at "5" regardless of a reduction in the first number of display frames. In this case, the first observation images may be displayed for only the time of the first two frames in the light emission period of the first illumination light, and the first observation images of the other three frames may be cancelled so that a period where the first observation image is not displayed is provided ("X" in the box shown in FIG. 13 represents that the first observation image is not displayed due to cancellation. The same applies to FIG. 15). Then, the second observation images are displayed for the time of all the five frames in the light emission period of the second illumination light.

Figure 14:
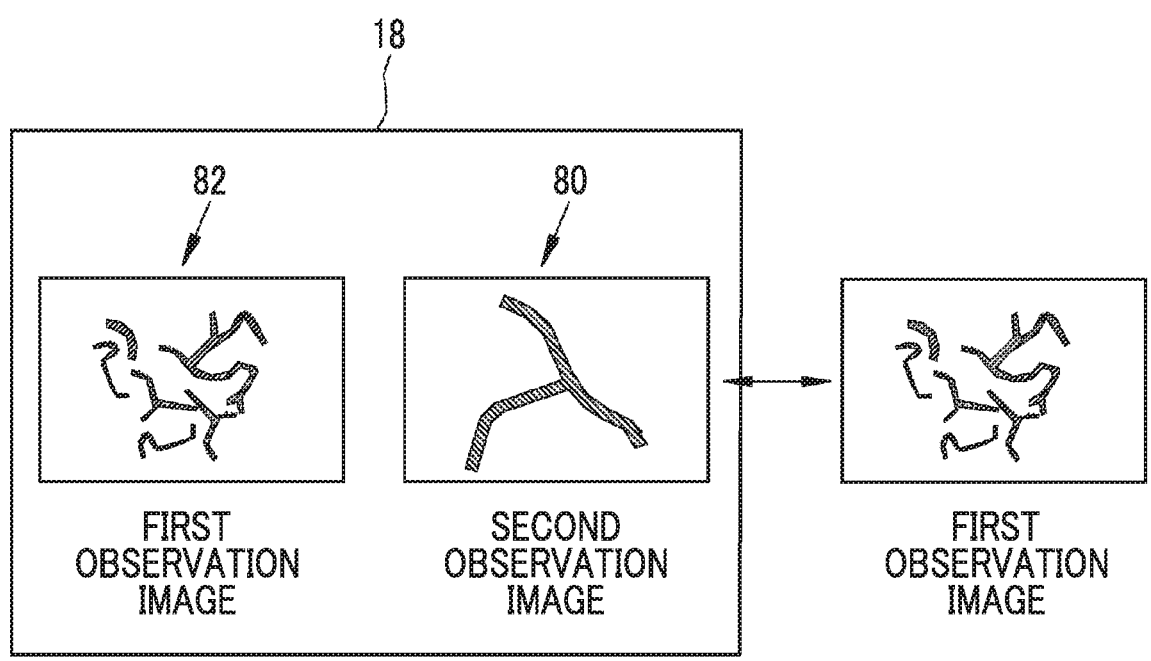
FIG. 14 is an image diagram of a monitor that includes a switching display screen and a single-image display screen.

Furthermore, in the above description, as shown in FIG. 14, the monitor 18 may be provided with a single-image display screen 82 where only any one of the first observation image or the second observation image is displayed (in FIG. 14, "first observation image" is displayed in the single-image display screen) in addition to a switching display screen 80 where the first observation image or the second observation image is displayed while being switched according to a specific display pattern. The number of display frames of the observation image, which is not to be displayed, of the first and second observation images is set to "0", so that only the observation image to be displayed is continuously displayed in the single-image display screen 82. The second number of display frames of the second observation image is set to "0" in FIG. 14, so that the first observation image is continuously displayed in the single-image display screen 82.

Figure 15:
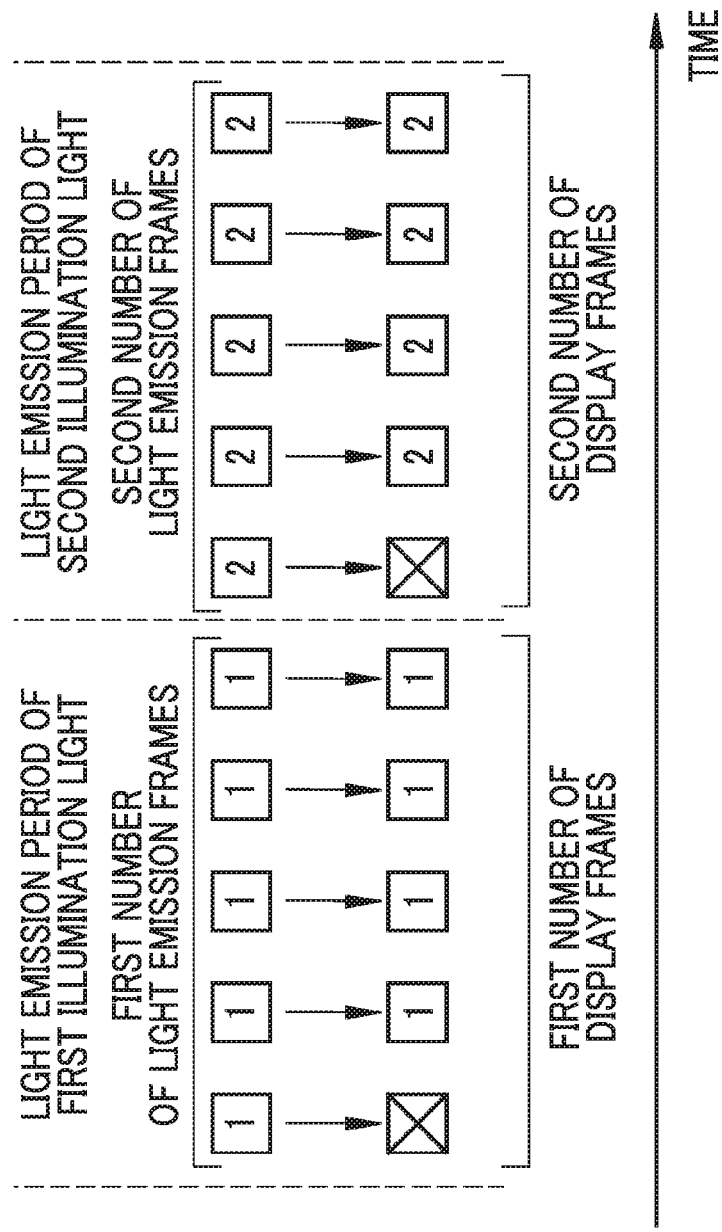
FIG. 15 is a diagram showing that a second observation image is not displayed immediately after switching.

Moreover, in the above description, the second observation image, which is obtained immediately after illumination light is switched to the second illumination light from the first illumination light, (the second observation image immediately after switching) is displayed as it is. However, since the second observation image immediately after switching is based on light where the first illumination light and the second illumination light are mixed, the second observation image immediately after switching is an image (an image where superficial blood vessels and medium-deep blood vessels are mixed) different from the original second observation image. For this reason, in a case where a user desires to clearly display a difference in specific subject information included in the first and second observation images, it is preferable that the second observation image immediately after switching (a second observation image obtained at the first frame in the light emission period of the second illumination light) is cancelled not to be displayed on the monitor 18 as shown in FIG. 15. Likewise, the first observation image, which is obtained immediately after illumination light is switched to the first illumination light from the second illumination light, may also be cancelled not to be displayed on the monitor 18.

Figure 16:
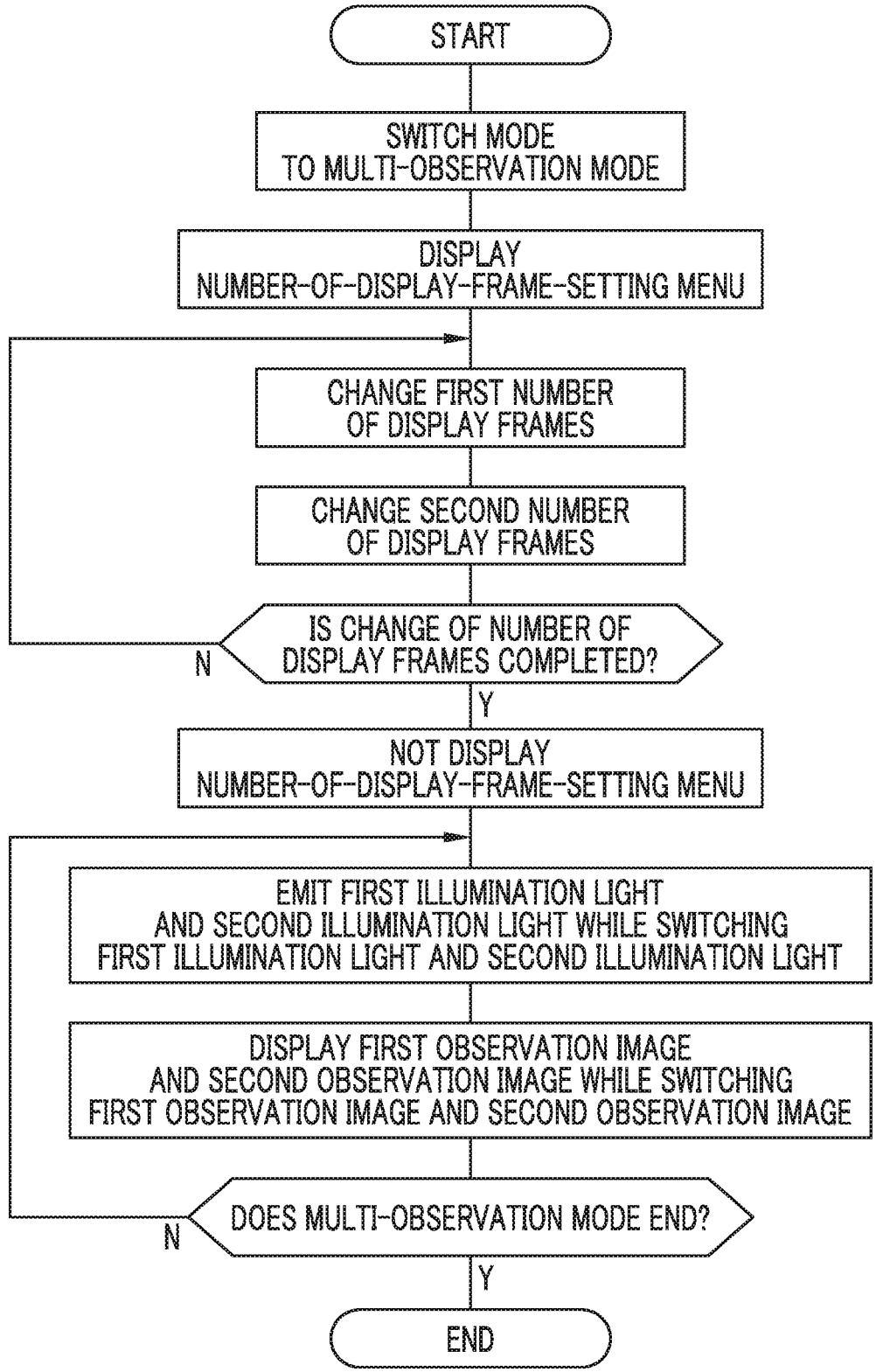
FIG. 16 is a flowchart showing the flow of a multi-observation mode.

Next, the multi-observation mode will be described along a flowchart of FIG. 16. In a case where a mode is switched to the multi-observation mode, the number-of-display-frame-setting menu 70 is displayed on the monitor 18. A user operates the user interface unit 19 to move the slider 72a to the left side or the right side on the slide bar 72, so that the first number of display frames of the first observation image is changed. Likewise, the user operates the user interface unit 19 to move the slider 74a to the left side or the right side on the slide bar 74, so that the second number of display frames of the second observation image is changed. Even though the first number of display frames or the second number of display frames is changed in this way, the first number of light emission frames of the first illumination light or the second number of light emission frames of the second illumination light is not changed.

After the user completes the change of the first number of display frames or the second number of display frames, the user operates the user interface unit 19 to end the setting of the number of display frames. Accordingly, the number-of-display-frame-setting menu 70 disappears from the monitor 18. Then, the multi-observation mode is performed. In accordance with this, the first illumination light is emitted for a time corresponding to the first number of light emission frames in a predetermined light emission cycle. After that, the first illumination light is switched to the second illumination light, and the second illumination light is emitted for a time corresponding to the second number of light emission frames. Further, in the light emission cycle, the first observation image based on the light emission of the first illumination light is displayed on the monitor 18 for a time corresponding to the first number of display frames. After that, the first observation image is switched to the second observation image, and the second observation image is displayed on the monitor 18 for a time corresponding to the second number of display frames. The light emission of the illumination light and the display of an object to be observed having been described above are repeatedly performed until the multi-observation mode ends.

In the embodiment, the first illumination light and the second illumination light have been emitted while being switched according to the specific light emission pattern, and the first observation image corresponding to the first illumination light and the second observation image corresponding to the second illumination light have been displayed on the monitor 18 while being switched according to the specific display pattern. However, three or more kinds of illumination light having wavelength ranges different from each other may be emitted while being switched according to a specific light emission pattern, and three or more kinds of observation images corresponding to the three or more kinds of illumination light may be displayed on the monitor 18 while being switched according to a specific display pattern.

Further, in the embodiment, as the specific light emission pattern, the first illumination light has been emitted for a time corresponding to the first number of light emission frames, the first illumination light then has been switched to the second illumination light, and the second illumination light has been emitted for a time corresponding to the second number of light emission frames in a predetermined light emission cycle. However, light may be emitted according to other light emission patterns. For example, in a case where third illumination light having a wavelength range between the wavelength of the first illumination light and the wavelength of the second illumination light is emitted in addition to the first illumination light and the second illumination light, as a specific light emission pattern, for example, the first illumination light, the third illumination light, and the second illumination light are emitted while being switched in this order and the number of light emission frames of any one of the first illumination light, the second illumination light, or the third illumination light is set to be larger than those of the other two.

Furthermore, in the embodiment, as the specific display pattern, the first observation image has been displayed on the monitor 18 for a time corresponding to the first number of display frames, the first observation image then has been switched to the second observation image, and the second observation image has been displayed on the monitor 18 for a time corresponding to the second number of display frames in a specific light emission cycle. However, images may be displayed according to other display patterns. For example, in a case where a third observation image obtained on the basis of third illumination light having a wavelength range between the wavelength of the first illumination light and the wavelength of the second illumination light is displayed in addition to the first observation image and the second observation image, as a specific display pattern, for example, the first observation image, the third observation image, and the second observation image are displayed while being switched in this order and the number of display frames of any one of the first observation image, the second observation image, or the third observation image is set to be larger than those of the other two.

The first number of display frames or the second number of display frames has been changed by a user in the embodiment, but the first number of display frames or the second number of display frames may be automatically changed on the basis of an observation image. For example, specific illumination light (of which the light intensities of violet light V and blue light B are higher than those of the other green light G and red light R), which can emphasize both superficial blood vessels and medium-deep blood vessels, is applied in addition to the first illumination light and the second illumination light, and a specific observation image, which is obtained in a case where an object to be observed is illuminated with the specific illumination light, is acquired. Then, a first difference image between the specific observation image and the first observation image and a second difference image between the specific observation image and the second observation image are obtained, and the first difference image and the second difference image are compared with each other. The first number of display frames and the second number of display frames may be determined on the basis of the result of this comparison.

For example, in a case where the first difference image has a pixel value (differential value) larger than the pixel value of the second difference image, many superficial blood vessels are included in the object to be observed. Accordingly, the first number of display frames or the second number of display frames is changed so that superficial blood vessels are emphasized. In contrast, in a case where the second difference image has a pixel value (differential value) larger than the pixel value of the first difference image, many medium-deep blood vessels are included in the object to be observed. Accordingly, the first number of display frames or the second number of display frames is changed so that medium-deep blood vessels are emphasized.

The hardware structures of the processing units, which are included in the processor device 16 in the embodiments, such as the image acquisition unit 53, the DSP 56, the noise removing unit 58, the image processing unit 60, the parameter switching unit 62, and the central control unit 68, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

[Additional claim 1]

An endoscope system comprising:

a plurality of semiconductor light sources that emit light having wavelength ranges different from each other;

a light source control unit that controls the semiconductor light sources, and performs control to emit a plurality of kinds of illumination light, which include first illumination light having a first light emission ratio and second illumination light having a second light emission ratio different from the first light emission ratio, while switching the plurality of kinds of illumination light according to a specific light emission pattern;

an image acquisition unit that acquires a plurality of observation images obtained from image pickup of an object to be observed illuminated with each illumination light, in which the plurality of observation images include a first observation image corresponding to the first illumination light and a second observation image corresponding to the second illumination light; and a display control unit that performs control to display the plurality of observation images on a display unit while switching the plurality of observation images according to a specific display pattern, wherein the specific light emission pattern is changeable and the specific display pattern is changeable.

[Additional claim 2]

The endoscope system according to Additional claim 1, wherein the specific light emission pattern is a pattern where the first illumination light is emitted for a time corresponding to the first number of light emission frames, the first illumination light is then switched to the second illumination light, and the second illumination light is emitted for a time corresponding to the second number of light emission frames in a predetermined specific light emission cycle, the specific display pattern is a pattern where the first observation image is displayed on the display unit for a time corresponding to the first number of display frames, the first observation image is then switched to the second observation image, and the second observation image is displayed on the display unit for a time corresponding to the second number of display frames in the specific light emission cycle, and the first number of light emission frames and the second number of light emission frames are changeable, and the first number of display frames and the second number of display frames are changeable.

EXPLANATION OF REFERENCES

10: endoscope system
12: endoscope
12a: insertion part
12b: operation part
12c: bendable part
12d: distal end part
12e: angle knobs
13b: display pattern switching unit
14: light source device
16: processor device
18: monitor
19: user interface unit
20: light source unit
20a: V-LED (violet light emitting diode)
20b: B-LED (blue light emitting diode)
20c: G-LED (green light emitting diode)
20d: R-LED (red light emitting diode)
21: light source control unit
23: optical path-combination unit
30a: illumination optical system
30b: image pickup optical system 41: light guide
45: illumination lens
46: objective lens
48: image pickup sensor
50: CDS/AGC circuit
53: image acquisition unit
56: digital signal processor (DSP)
58: noise removing unit
60: image processing unit
62: parameter switching unit
66: display control unit
68: central control unit
70: number-of-display-frame-setting menu
72: slide bar
72a: slider
74: slide bar
74a: slider
80: switching display screen
82: single-image display screen

What is claimed is:

1. An endoscope system comprising:
a plurality of semiconductor light sources that emit light having wavelength ranges different from each other;
a light source controller that controls the plurality of semiconductor light sources, and performs control to emit a plurality of kinds of illumination light, which include first illumination light having a first light emission ratio and second illumination light having a second light emission ratio different from the first light emission ratio, while switching the plurality of kinds of illumination light according to a specific light emission cycle;
a processor configured to function as:
an image acquisition circuit that acquires a plurality of observation images obtained from image pickup of an object to be observed illuminated with each illumination light, in which the plurality of observation images include a first observation image corresponding to the first illumination light and a second observation image corresponding to the second illumination light; and
a display control circuit that performs control to display the plurality of observation images on a display while switching the plurality of observation images according to a specific display cycle, the specific display cycle being carried out in real time,
wherein the plurality of kinds of illumination light includes specific illumination light which can emphasize both superficial blood vessels and medium-deep blood vessels,
wherein the specific display cycle is determined on the basis of the result of comparison between a first difference image between a specific observation image obtained by illuminating the object to be observed with the specific illumination light and the first observation image and a second difference image between the specific observation image and the second observation image, in synchronization with the light emission cycle,
wherein, in the specific display cycle, after displaying the first observation image, not in synchronization with the light emission cycle, on the display for a time corresponding to a first number of display frames, the second observation image is displayed, not in synchronization with the light emission cycle, on the display for a time corresponding to a second number of display frames,
wherein setting the first number of display frames larger than the second number of display frames and setting the first number of display frames smaller than the second number of display frames are switchable without changing the light emission cycle,
wherein in a case where the first difference image has a pixel value larger than a pixel value of the second difference image, the first number of display frames or the second number of display frames is changed so that the superficial blood vessels are emphasized, and
wherein in a case where the second difference image has the pixel value larger than the pixel value of the first difference image, the first number of display frames or the second number of display frames is changed so that the medium-deep blood vessels are emphasized.

2. The endoscope system according to claim 1,
wherein gain processing for first illumination light or structure emphasis processing for first illumination light applied to the first observation image and gain processing for second illumination light or structure emphasis processing for second illumination light applied to the second observation image are switched, in synchronization with the light emission cycle, with the switching between the first illumination light and the second illumination light,
wherein the specific light emission cycle is fixed and the specific display cycle is changeable.

3. The endoscope system according to claim 2,
wherein the specific light emission cycle is a pattern where the first illumination light is emitted for a time corresponding to a first number of light emission frames, the first illumination light is then switched to the second illumination light, and the second illumination light is emitted for a time corresponding to a second number of light emission frames in a predetermined specific light emission cycle,
the specific display cycle is a cycle where the first observation image is displayed on the display for the time corresponding to the first number of display frames, the first observation image is then switched to the second observation image, and the second observation image is displayed on the display for the time corresponding to the second number of display frames in the specific light emission cycle, and
the first number of light emission frames and the second number of light emission frames are fixed, and the first number of display frames and the second number of display frames are changeable.

4. The endoscope system according to claim 3,
wherein in a case where a first display pattern where the first number of display frames is set to be larger than the second number of display frames is set, a first observation image within a second illumination light-emission period, which is displayed on the display in a light emission period of the second illumination light, is displayed on the basis of a first observation image within a first illumination light-emission period that is obtained in a light emission period of the first illumination light prior to the light emission period of the second illumination light.

5. The endoscope system according to claim 3,
wherein in a case where a second display pattern where the first number of display frames is set to be smaller than the second number of display frames is set, a second observation image within a first illumination light-emission period, which is displayed on the display in a light emission period of the first illumination light, is displayed on the basis of a second observation image within a second illumination light-emission period that is obtained in a light emission period of the second illumination light prior to the light emission period of the first illumination light.

6. The endoscope system according to claim 3, wherein in a case where a second display pattern where the first number of display frames is set to be smaller than the second number of display frames is set, the first observation image is not displayed on the display in a light emission period of the first illumination light.

7. The endoscope system according to claim 3, further comprising:
a display pattern switching circuit that is used to switch a first display pattern where the first number of display frames is set to be larger than the second number of display frames and a second display pattern where the first number of display frames is set to be smaller than the second number of display frames.

8. The endoscope system according to claim 2, wherein the display displays a switching display screen that displays the plurality of observation images while switching the plurality of observation images and a single-image display screen that displays only any one of the plurality of observation images.

9. The endoscope system according to claim 8, wherein in a case where only any one of the first observation image or the second observation image is displayed in the single-image display screen, a number of display frames of the observation image that is not displayed, which is not displayed in the single-image display screen, of the first and second observation images is set to "0".

10. The endoscope system according to claim 2, wherein the display control circuit cancels an observation image from amongst the plurality of observation images immediately after switching, which is obtained immediately after switching of each illumination light, not to display the observation image on the display.

11. The endoscope system according to claim 2, wherein the processor performs mucous membrane-color-balance processing for setting the colors of mucous membranes, which are included in the object to be observed, to the same color between the first observation image and the second observation image.

12. A method of operating an endoscope system comprising:
a light source control step of causing a light source controller, which controls a plurality of semiconductor light sources emitting light having wavelength ranges different from each other, to perform control to emit a plurality of kinds of illumination light, which include first illumination light having a first light emission ratio and second illumination light having a second light emission ratio different from the first light emission ratio, while switching the plurality of kinds of illumination light according to a specific light emission cycle;
an image acquisition step of causing a processor to acquire a plurality of observation images obtained from image pickup of an object to be observed illuminated with each illumination light, in which the plurality of observation images include a first observation image corresponding to the first illumination light and a second observation image corresponding to the second illumination light; and
a display control step of causing the processor to perform control to display the plurality of observation images on a display while switching the plurality of observation images according to a specific display cycle, the specific display cycle being carried out in real time,
wherein gain processing for first illumination light or structure emphasis processing for first illumination light applied to the first observation image and gain processing for second illumination light or structure emphasis processing for second illumination light applied to the second observation image are switched, in synchronization with the light emission cycle, with the switching between the first illumination light and the second illumination light, and
wherein the specific light emission cycle is fixed and the specific display cycle is changeable,
wherein, in the specific display cycle, after displaying the first observation image, not in synchronization with the light emission cycle, on the display for a time corresponding to a first number of display frames, the second observation image is displayed, not in synchronization with the light emission cycle, on the display for a time corresponding to a second number of display frames,
wherein setting the first number of display frames larger than the second number of display frames and setting the first number of display frames smaller than the second number of display frames are switchable without changing the light emission cycle,
wherein the plurality of kinds of illumination light includes specific illumination light which can emphasize both superficial blood vessels and medium-deep blood vessels,
wherein the specific display cycle is determined on the basis of the result of comparison between a first difference image between a specific observation image obtained by illuminating the object to be observed with the specific illumination light and the first observation image and a second difference image between the specific observation image and the second observation image, in synchronization with the light emission cycle,
wherein in a case where the first difference image has a pixel value larger than a pixel value of the second difference image, the first number of display frames or the second number of display frames is changed so that the superficial blood vessels are emphasized, and
wherein in a case where the second difference image has the pixel value larger than the pixel value of the first difference image, the first number of display frames or the second number of display frames is changed so that the medium-deep blood vessels are emphasized.

* * * * *